(12) United States Patent
Iyengar et al.

(10) Patent No.: US 9,572,524 B2
(45) Date of Patent: Feb. 21, 2017

(54) METHOD AND APPARATUS FOR ASSAY OF ELECTROCHEMICAL PROPERTIES

(71) Applicant: AGAMATRIX, INC., Salem, NH (US)

(72) Inventors: Sridhar G. Iyengar, Salem, NH (US); Ian S. Harding, Wells (GB)

(73) Assignee: AgaMatrix, Inc., Salem, NH (US)

( * ) Notice: Subject to any disclaimer, the term of this patent is extended or adjusted under 35 U.S.C. 154(b) by 0 days.

(21) Appl. No.: 14/919,935

(22) Filed: Oct. 22, 2015

(65) Prior Publication Data

US 2016/0038063 A1    Feb. 11, 2016

Related U.S. Application Data

(63) Continuation of application No. 14/622,415, filed on Feb. 13, 2015, now Pat. No. 9,188,525, which is a
(Continued)

(51) Int. Cl.
| | | |
|---|---|---|
| *G01N 27/327* | (2006.01) | |
| *G01N 27/30* | (2006.01) | |
| *A61B 5/1495* | (2006.01) | |
| *G01N 27/26* | (2006.01) | |
| *A61B 5/1468* | (2006.01) | |

(Continued)

(52) U.S. Cl.
CPC .......... *A61B 5/1495* (2013.01); *A61B 5/1468* (2013.01); *A61B 5/1473* (2013.01); *A61B 5/7203* (2013.01); *G01N 17/02* (2013.01); *G01N 27/26* (2013.01); *G01N 27/3273* (2013.01); *G01N 27/3274* (2013.01); *A61B 2562/04* (2013.01)

(58) Field of Classification Search
CPC . G01N 27/327–27/3274; A61B 5/1473; A61B 5/14735; A61B 5/1486; A61B 5/14865
See application file for complete search history.

(56) References Cited

U.S. PATENT DOCUMENTS

| | | |
|---|---|---|
| 3,644,824 A | 2/1972 | Barker et al. |
| 4,419,190 A | 12/1983 | Dietz et al. |
| (Continued) | | |

FOREIGN PATENT DOCUMENTS

| | | |
|---|---|---|
| WO | 9739343 A1 | 10/1997 |
| WO | 9932881 | 7/1999 |
| (Continued) | | |

OTHER PUBLICATIONS

Iyengar et al., Data from overlapping signals at an amperometric electrode using admittance vectors, Journal of Electroanalytical Chemistry, 2002, pp. 61-71, vol. 521, www.elsevier.com/locate/jelemchem, XP002569189.
(Continued)

*Primary Examiner* — Alexander Noguerola
(74) *Attorney, Agent, or Firm* — Larson & Anderson, LLC

(57) ABSTRACT

A method for monitoring a select analyte in a sample in an electrochemical system. The method includes applying to the electrochemical system a time-varying potential superimposed on a DC potential to generate a signal; and discerning from the signal a contribution from the select analyte by resolving an estimation equation based on a Faradaic signal component and a nonfaradaic signal component.

8 Claims, 19 Drawing Sheets

Related U.S. Application Data continuation of application No. 13/654,668, filed on Oct. 18, 2012, now abandoned, which is a continuation of application No. 12/576,631, filed on Oct. 9, 2009, now Pat. No. 8,293,094, which is a continuation of application No. 10/504,199, filed as application No. PCT/US03/04024 on Feb. 10, 2003, now Pat. No. 7,601,249.

(60) Provisional application No. 60/355,866, filed on Feb. 10, 2002.

(51) Int. Cl.
  *G01N 17/02* (2006.01)
  *A61B 5/1473* (2006.01)
  *A61B 5/00* (2006.01)

(56) References Cited

U.S. PATENT DOCUMENTS

| | | |
|---|---|---|
| 4,566,949 A | 1/1986 | Berger |
| 4,919,770 A | 4/1990 | Preidel et al. |
| 5,180,968 A | 1/1993 | Bruckenstein et al. |
| 5,423,963 A | 6/1995 | Fletcher et al. |
| 5,438,271 A | 8/1995 | White et al. |
| 6,275,717 B1 | 8/2001 | Gross et al. |
| 6,645,368 B1 | 11/2003 | Beaty et al. |
| 9,188,525 B2 * | 11/2015 | Iyengar .............. G01N 27/3273 |
| 2003/0098233 A1 | 5/2003 | Kermani et al. |
| 2003/0106809 A1 | 6/2003 | Kermani et al. |
| 2003/0178322 A1 | 9/2003 | Iyengar et al. |
| 2004/0157338 A1 | 8/2004 | Burke et al. |
| 2004/0157339 A1 | 8/2004 | Burke et al. |
| 2005/0023154 A1 | 2/2005 | Kermani et al. |
| 2005/0067301 A1 | 3/2005 | Morita et al. |

FOREIGN PATENT DOCUMENTS

| | | |
|---|---|---|
| WO | 03060154 A2 | 7/2003 |
| WO | 2005022143 A2 | 3/2005 |

OTHER PUBLICATIONS

Iyengar et al., Phasor transform to extract glucose and ascorbic acid data in an amperometric sensor, Analyst, 2000, pp. 1987-1992, vol. 125, No. 11, Royal Society of Chemistry, GB, XP009104740.

\* cited by examiner

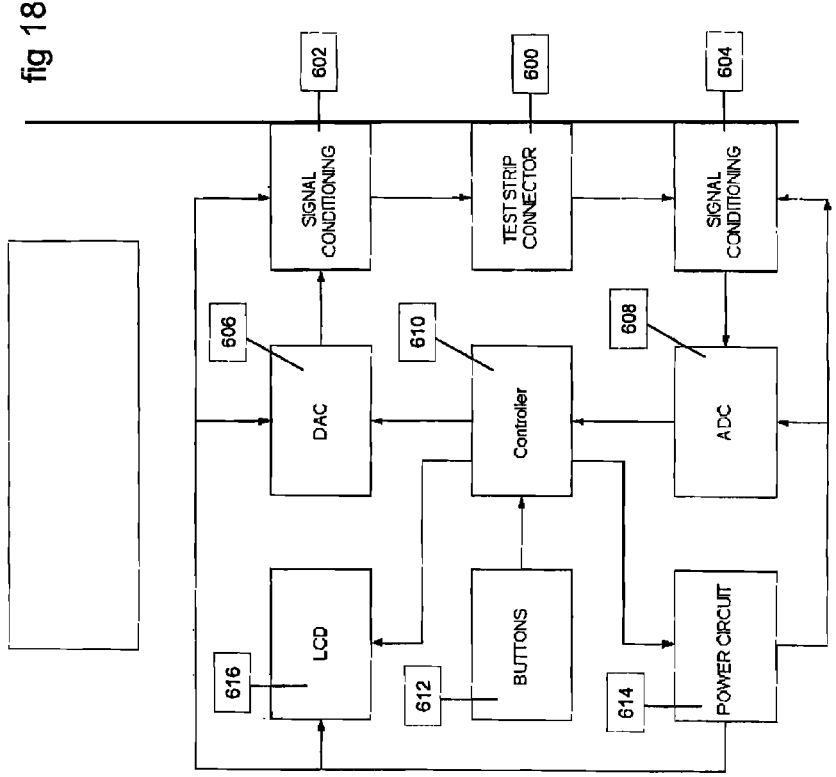

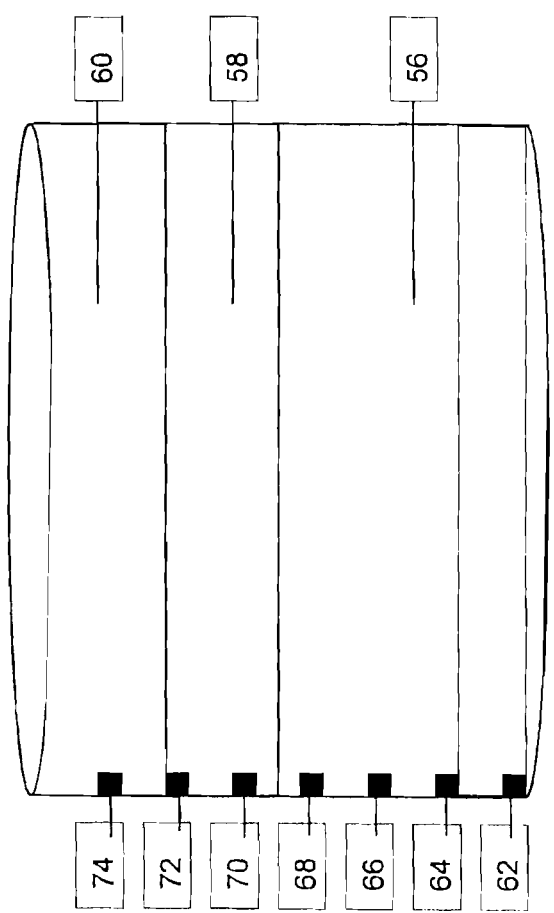

METHOD AND APPARATUS FOR ASSAY OF ELECTROCHEMICAL PROPERTIES

BACKGROUND

The use of electrochemical means of detection has often been chosen for its simplicity, both in terms of device manufacture and in terms of ease of use. The principle mode of selectivity of electrochemistry (both for amperometric and potentiometric modes) is the reduction-oxidation (also called "redox") potential of the analyte (which is the chemical species of electrochemical interest). For example, using the technique of amperometry (where the potential is applied to the electrode, and the resulting current is measured), the selectivity towards the analyte is achieved based on the redox potential of the analyte.

The signal that is generated at the electrode can depend on many factors and properties of the electrochemical system. Examples of properties of the sample that affect the transport of the analyte include viscosity, temperature, density, and ionic strength. The variations that affect the transport of the analyte can subsequently affect the measured electrochemical signal. Examples of such transport mechanisms include diffusion, migration, and convection.

In another example, the properties of the electrode itself can affect the transport of the analytes and/or the kinetics of any reactions that may generate the measured electrochemical signals. Examples of such properties include the effective electrode area, the geometry of the electrodes, the geometry of the sample chamber, the extent of electrode fouling, diffusional barrier membranes over the electrode, and catalytic properties of the electrode material.

Electrochemical sensors are commonly found in a number of sensing applications, from medical biosensors to environmental and gas sensors. There are commonly two modes of electrochemical measurement, amperometric and potentiometric. Amperometric sensors operate on the principle of applying a voltage potential to an electrode and measuring the resulting current. Examples of amperometric sensors include most commercial glucose biosensors and many gas sensors. Potentiometric sensors operate on the principle of applying a current to an electrode and measuring the resulting potential. It is often the case that the applied current is kept at zero amps. The pH electrode is an example of a potentiometric sensor.

FIG. 1 shows the action of an amperometric sensor in which a voltage is applied to the electrode 310 which causes a particular analyte (the substance being measured) in the sample to be oxidized (i.e., giving up electrons to the electrode). The oxidation causes a current 315 to be generated which can then be detected and analyzed. The potential at which the analyte oxidizes is called the "oxidation potential" of the analyte.

Generally speaking, the term "redox potential" is used to indicate the potential at which an analyte is either oxidized or reduced. In the sensor of FIG. 1, ferrocyanide ("FERRO") 300 transfers electrons to the electrode if the potential is high enough to cause the electrochemical reaction to occur. Once the electrons are transferred, ferrocyanide is oxidized to ferricyanide ("FERRI") 305.

Thus, in FIG. 1, a sufficiently high potential is being applied to oxidize ferrocyanide, the reduced form of the electroactive species, to the oxidized form, ferricyanide, and the resultant current 315 detected by the electrode depends on the concentration of the reduced species.

As discussed above, the current from amperometric sensors depends on a number of factors in addition to the concentration of the analyte of interest. Traditional amperometric methods rely on the assumption that only the concentration of the analyte changes from measurement to measurement; hence, when other factors of the electrochemical system vary, the measured signal and the estimate of the analyte concentration can be incorrect. Potentiometric sensors also suffer from related factors, including transport of the analyte and electrode fouling. Variations in these factors would add uncertainty and error to the measured signal. For example, FIG. 2 shows the DC current from two amperometric sensors where the effective electrode area is changed. Data points 455 are measured in a sample containing 10 mM ferrocyanide. Data points 450 are measured in a sample containing 20 mM ferrocyanide. In both cases, as the electrode area varies, the measured DC current signal varies as well. Furthermore, for a given electrode area, increasing the analyte concentration from 10 mM to 20 mM results in measuring an increased current signal. This illustrates the dependence of the measured DC current signal on the electrode area and on the analyte concentration.

Several factors may contribute to a sensor having variable electrode area. One source may be errors during manufacturing that may lead to variability in the electrode area from sensor to sensor. Another factor may be deterioration of the electrode during use. Another factor may be incomplete contact of the sample with the sensor electrode, examples of which are illustrated in FIGS. 8 and 9.

FIGS. 8a through 8c are schematic diagrams of a typical electrochemical test strip that forms the basis for many commercially available glucose biosensors. In FIG. 8a, there are two electrodes 355, each of which is connected to leads 350 that interface with the electronics of the meter. The electrodes 355 and leads 350 may be coupled to a support substrate 375. In this example, the test strip uses a commonly used 2-electrode configuration. In FIG. 8a, the sample 360 completely covers both electrodes, ensuring that the entire electrode area of each electrode is in contact with the sample. In FIG. 8b, sample 370 covers one electrode completely but partially covers the other electrode. In FIG. 8c, sample 365 partially covers both electrodes.

FIG. 9 illustrates partial coverage of electrodes by a sample for a different geometry of electrodes. In this example, an electrochemical test strip is made with two electrodes facing each other in a parallel plate design. Electrode 400 and electrode 405 are supported by a solid substrate material 420. Sample 410 fills the sample chamber and covers both electrode areas fully. Sample 415, however, only partially covers both electrode areas and results in a system of reduced effective electrode area. Such incomplete coverage of the electrode surface can be a result of partial filling of the sample chamber. In one example, diabetic patients that make blood glucose measurements must often use such electrochemical test strips to make measurements of blood glucose. In such cases, if enough blood does not enter into the sample chamber, incomplete coverage of the electrode system can result, yielding inaccurate glucose estimates. Thus, a method to assess the effective electrode area that is independent of the analyte concentration would be useful.

Furthermore, the volume of sample that enters into the test strip can be estimated. Referring to FIG. 9, if the three dimensions of the sample chamber that contains sample 415 are known, then the volume of sample 415 can be estimated by scaling the total geometric volume of the sample chamber by the fractional amount of the electrode coverage. In one example, the total volume of the sample chamber is 100 nL. If sample 415 is determined to cover 75% of the electrode 405, then one estimate of the volume of sample 415 would be (0.75)*100 nL=75 nL. The estimate of the sample volume would be useful when making measurements that depend on knowing the volume of the sample in the electrochemical cell. One example of where this knowledge would be useful is in coulometry.

FIG. 4 illustrates the problem of electrode fouling with electrochemical sensors. Electrode fouling, also called sensor fouling, is a term that describes material 320 adhering, adsorbing, or otherwise coating all or part of the electrode 310. In this example, the analyte is ferrocyanide 300 which must move through the fouling material 320 and then react at the electrode 320 in an oxidation reaction that yields an electronic current 315 in the electrode 310. The product of the reaction is ferricyanide 305 which then moves back out of the fouling material 320. One example of when electrode fouling may occur is during extended use of the sensor in environments that could cause fouling, such as implanting a biosensor into the body or deploying gas sensors in environments containing sulfides. In such situations, as well as other situations that would be apparent to one skilled in the art, material may deposit onto the electrode, causing a distorted signal to be measured. Often, the measured signal intensity decreases as the amount of electrode fouling increases until ultimately the sensor becomes insensitive to the target analyte. In other cases, the fouling material may act as a catalyst for certain chemical reactions and the sensor's response may actually be enhanced. In either case, if the sensor's response is altered due to fouling, then the resulting measurement is inaccurate.

In the calibration curves shown in FIG. 3, data points 470 measure the DC current from samples with different concentrations of ferrocyanide with an electrode that is not fouled. Data points 480 measure the DC current from samples with different concentrations of ferrocyanide with an electrode that is fouled by a coating of 3.33 µg of cellulose acetate. Data points 490 measure the DC current from samples with different concentrations of ferrocyanide with an electrode that is fouled by a coating of 10 µg of cellulose acetate. This example illustrates that the measured DC current signal in this amperometric sensor depends on both the analyte concentration and the extent of electrode fouling. Thus, a low DC signal may be the result of either low analyte concentration or due to increased electrode fouling. Thus, a means to determine the extent of electrode fouling which is independent of analyte concentration would be useful. Such a method could then be used to adjust the measured current signal and correct for signal distortion caused by electrode fouling.

Although the previous two examples were illustrated with amperometric sensors, one of ordinary skill in the art will recognize the application to potentiometric sensors. Potentiometric sensors also rely on analyte coming into the proximity of the electrode.

Thus, when electrochemical means of detection are used, the environmental factors—including the properties of the sample that contain the analyte—may heavily influence the signal that is measured. Such factors may introduce inaccuracies into the measurement, including but not limited to, change in calibration and change in sensitivity. Hence a method and apparatus for detecting properties of the environment that may affect the measured signal, including dielectric constant of the sample or the electrode, effective electrode area, and ionic strength of the sample, would benefit electrochemical sensor systems and may allow for corrections to be made to the estimated analyte concentration, calculated from the measured signal, based on the information about the environmental factors.

SUMMARY OF THE INVENTION

An embodiment of the present invention relates to a method for monitoring a select analyte in a sample in an electrochemical system. The method includes applying to the electrochemical system a time-varying potential superimposed on a DC potential to generate a signal; and discerning from the signal a contribution from the select analyte by resolving an estimation equation based on a Faradaic signal component and a nonfaradaic signal component.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 18 is a glucose meter in accordance with an illustrative embodiment; and FIG. 19 is an illustration of a fuel tank containing spatially separated layers of petrol and water.

DETAILED DESCRIPTION

Figure 1:
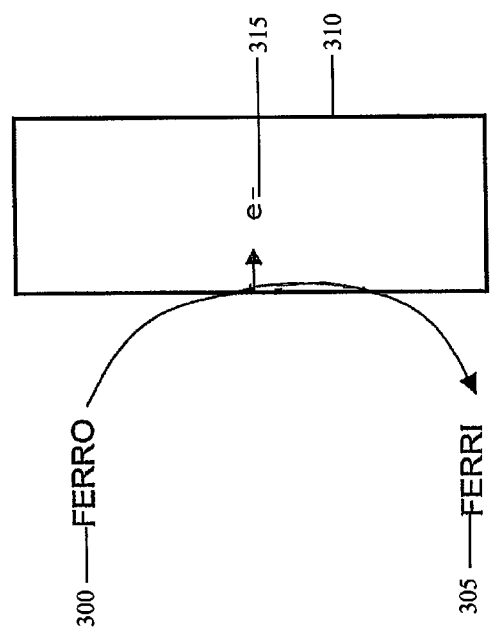
FIG. 1 is an amperometric sensor for measuring ferrocyanide.

Reference will now be made in detail to several illustrative embodiments of the present invention, examples of which are shown in the accompanying drawings. Wherever possible, the same reference numbers will be used throughout the drawings to refer to the same or like parts.

Systems and methods are provided herein for improving the accuracy and productivity of sensors via digital signal processing techniques. In particular, in accordance with certain illustrative embodiments, methods are provided herein for monitoring environmental effects that can affect the measured sensor signal, e.g. effective electrode area and/or extent of fouling, to correct for measurement errors. In this way, a change in the measured signal that is due to an environmental factor can be substantially reduced to more accurately measure the concentration of a target analyte, such as ferrocyanide.

As used herein, the term "transducer" refers to a substance or apparatus that converts energy of one form into energy of another form. Examples of transducers include, but are not limited to, electrodes, light emitting diodes, photo diodes, piezoelectric material, and microphones.

As used herein, the term "capacitive properties" refers to any and all properties of a system that may contribute and/or affect the capacitance of the system and includes, but is not limited to, the electrode area, the dielectric constant, the permittivity, double-layer characteristics, ionic strength of a sample, and the capacitance.

As used herein, the term "blank" refers to a sample that is comprised of supporting electrolyte.

As used herein, the term "background" can be used interchangeably with the term "blank" and refers to the signal that is generated by a blank sample.

As used herein, the term "CDAS" refers to capacitive dominated admittance spectra and indicates the frequency range in which the admittance values of the electrochemical system is dominated by the capacitive components of the electrochemical system; this may generally be towards the higher frequency range but may be in other ranges depending on the characteristics of the particular electrochemical system under consideration.

As used herein, the term "ESS" refers to an electrochemical signal source, which is an entity in a sample that can give rise to an electrochemical signal; the term "ESSs" is used to refer to the plural of ESS. A common ESS is an electroactive chemical species, but the invention is not limited to the assay of signals only from such sources and includes non-electroactive chemical species, background electrolyte, double-layer capacitance, non-chemical sources, and sources not in the sample such as electromagnetic interference, commonly known as RF interference.

As used herein, the term "ESSI" refers to an ESS that is of interest to be measured including, but not limited to, chemical species, or the background composition of a sample that may give rise to the background or blank signal, or the capacitance that may be measured by the transducer-sample interface.

The term "variation" as used herein, refers to the absolute value of the difference between the maximum value and the minimum value of a waveform during the course of its application.

As used herein, the term "TSI" refers to the transducer-sample interface that is comprised of the interface between the transducer and the sample that may contain a set of ESSs.

As used herein, the term "FFT" refers to Fast Fourier Transform.

As used herein, the term "FT" refers to Fourier Transform.

As used herein, the term "DFT" refers to discrete Fourier Transform.

As used herein, the term "WT" refers to Wavelet Transform.

As used herein, the term "DTFT" refers to discrete time Fourier Transform.

As used herein, the term "ADC" refers to an analog-to-digital converter.

As used herein, the term "derived quantities" refers to quantities that may be computed with reference to the measured data from the electrochemical system and external sources of data and/or information.

As used herein, the term "Faradaic" refers to electrochemical reactions in which electronic charge is transferred across the TSI. These reactions refer to an oxidation or reduction of an analyte.

As used herein, the term "effective electrode area" refers to the electrode area that is in electrolytic contact with the sample. The effective electrode area may be varied by altering the geometry of the electrode or by partial contact of the electrode to the sample.

As used herein, the term "extent of electrode fouling" refers to the amount, geometry, density, and/or composition of material that may adsorb or otherwise coat all or part of an electrode or sensor.

As used herein, the term "environmental factors" refers to properties and/or factors other than the analyte concentration that affect the measured electrochemical signal. Examples include, but are not limited to, electrode area, extent of electrode fouling, dielectric of the sample, temperature, and ionic concentration of the sample.

As used herein, the term "electrolytic contact" refers to having an electrochemical system comprised of at least one electrode deployed in a manner so as to gather electrochemical information from a sample. Examples include, but are not limited to, an electrode in physical contact with a sample; an electrode separated from a sample by a membrane, a film, or other material; and an electrode separated from a sample by an aqueous medium. Examples of electrochemical information include Faradaic current, nonfaradaic current, and chemical potential.

As used herein, the term "electrochemical system" refers to a system comprised of at least one electrode used to gather electrochemical data. Examples of electrochemical systems include two-electrode configurations; three-electrode configurations; and electrode arrays.

As used herein, the term "electrode set" refers to an electrochemical system comprised of at least one electrode.

As used herein, the term "spectral analysis" refers to a method of analyzing the spectral content of a signal or portion of a signal. Examples of methods used for spectral analysis include FT, FFT, DFT, DTFT, and WT.

Figure 5:
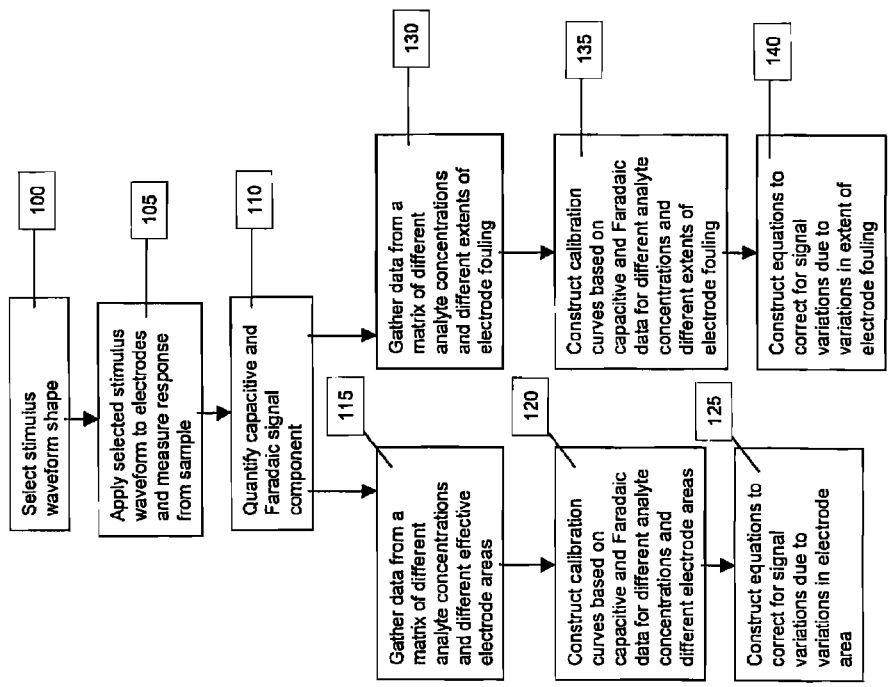
FIG. 5 is a flow diagram illustrating a method for processing electrochemical signals in accordance with an illustrative embodiment.
Figure 6:
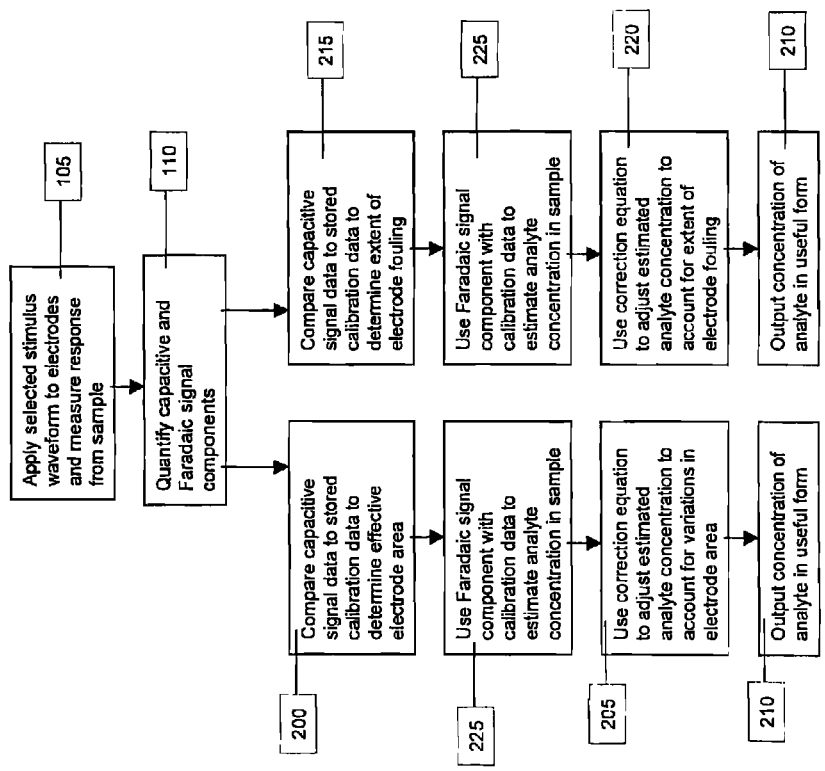
FIG. 6 is a flow diagram illustrating a method for processing electrochemical signals in accordance with another illustrative embodiment.
Figure 7:
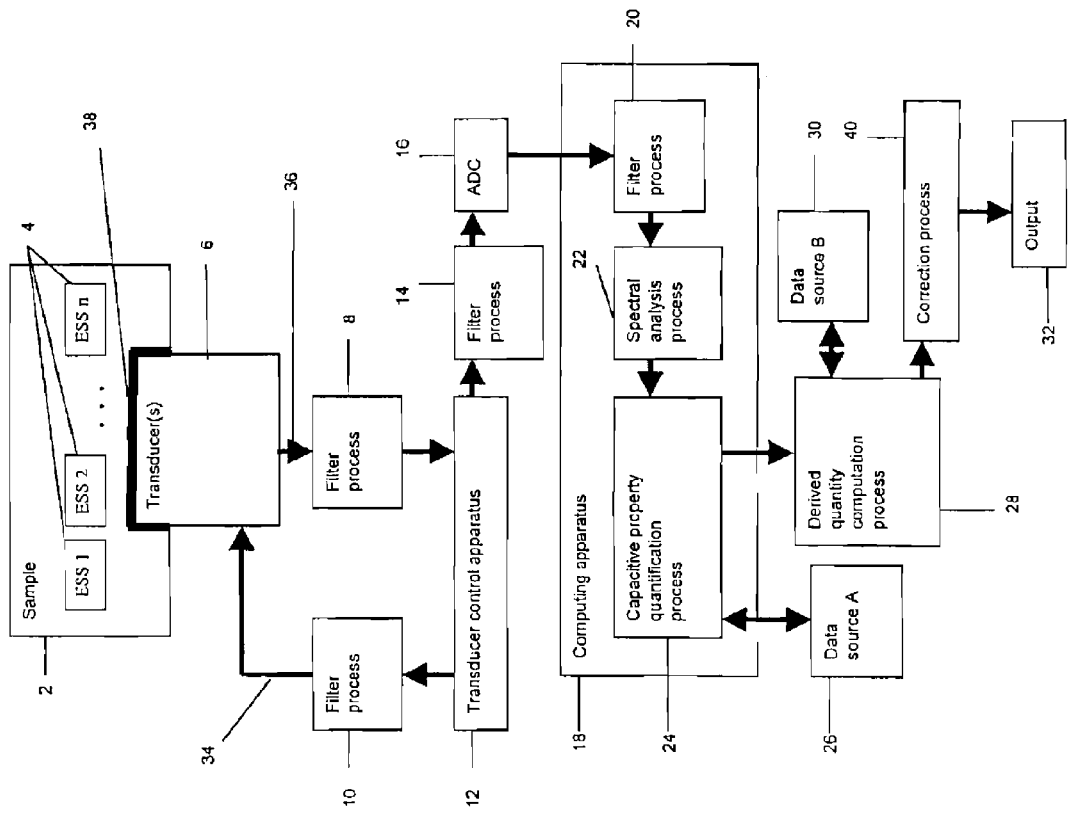
FIG. 7 is a system for processing electrochemical signals in accordance with another illustrative embodiment.
Figure 8:
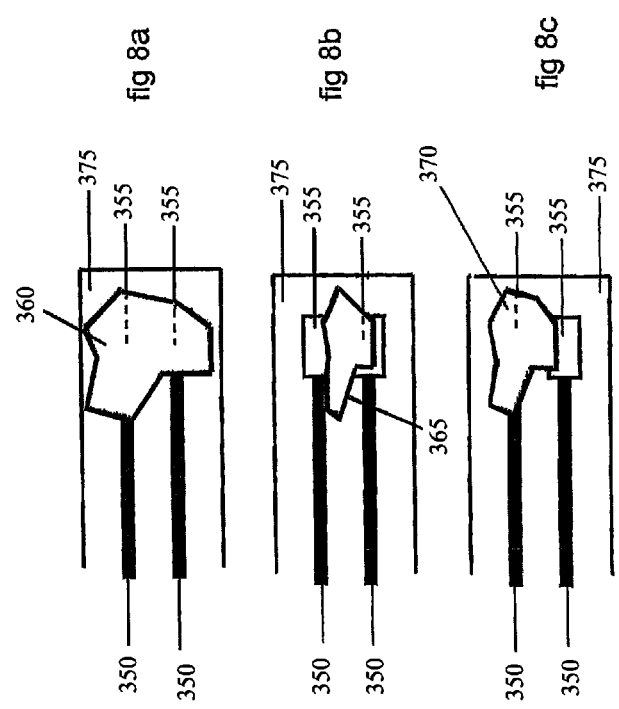
FIGS. 8a, 8b, and 8c show three examples of how a sample can make contact with electrodes for one particular geometric organization of electrodes.
Figure 9:
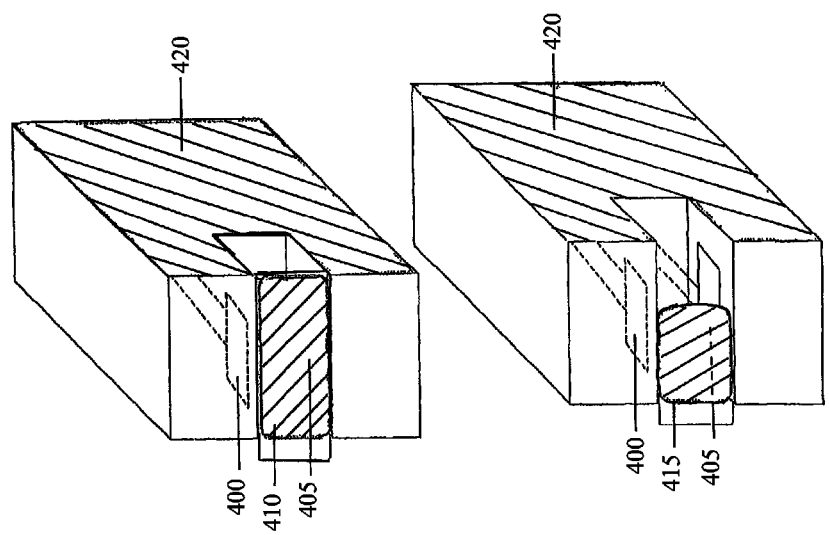
FIG. 9 shows two examples of how a sample can make contact with electrodes for another particular geometric organization of electrodes.

FIGS. 5-7 show an illustrative embodiment of a method and system for determining the signal variation due to environmental factors that alter an electrochemical signal in response to an applied voltage waveform. For example, signal variations caused by environmental factors may be quantified and corrected, if necessary, by altering the apparent measured analyte concentration estimate. FIGS. 5 and 6 illustrate embodiments of the method in flow diagram form.

FIG. 7 shows a more detailed example of a system for carrying out the methods of FIGS. 5 and 6, but it should be understood that the methods of FIGS. 5 and 6 could be implemented by any number of different systems and apparatus. For example, the system of FIG. 7 could in turn be implemented as a handheld tester, such as for testing glucose concentrations in blood.

FIG. 7 illustrates an exemplary method for identifying and quantifying the capacitive properties of the TSI according to an embodiment of the present invention. All arrows represent a set of communication channels, unless otherwise labeled, and can include but are not limited to, electrical transmission via physical conductors, wireless transmission, and multiple channels of communication. The following steps outline one exemplary apparatus and one exemplary process that illustrates the invention.

1. A set of appropriate transducers 6 is deployed in a manner that is appropriate for detecting ESSs 4 in a sample 2. In this example, the transducers 6 are electrodes that are placed in electrolytic contact at the transducer-sample interface 38 with a sample 2 containing multiple ESSs 4, labeled as ESS 1, ESS2 and ESS n, where n signifies a number that represents an ESS that is unique from the other ESSs in the sample 2. Other examples of transducers may include electrodes with membranes, chemically-modified electrodes, or other elements that can be used as electrochemical transducers.

2. A control signal 34 is applied to transducer 6 from a transducer control apparatus 12 which may be processed by an optional filtering process 10 such as a circuit or a computation apparatus that executes the filtering process. The filtering process 10 may be part of the transducer control apparatus 12. One benefit of a filter would be to remove unwanted noise from the applied signal. In this embodiment, the control signal 34 is a voltage potential waveform that is applied by a transducer control apparatus 12 in the form of a potentiostat circuit. A potentiostat is a circuit that is commonly used to control and record electrochemical data and is explained in "Electrochemistry: Principles, Methods, and Applications", 1$^{st}$ ed. Oxford University Press, 1993 by C. M. A. Brett and A. M. O. Brett.

3. The time-domain signal 36 (that is, the current signal that is generated, as a function of time) from the transducers 6 with the transducer control apparatus 12 is measured and, if needed, is stored. An optional filtering process 8 may be part of this process, and furthermore may be part of the transducer control apparatus 12. The filtering process may be analogous to figure item 10 and would provide the useful benefit of removing unwanted signal noise.

4. The signal is optionally filtered using a filtering process 14. One example of such a filter includes an anti-aliasing filter used in conjunction with the process of converting analog signals to digital signals. Other examples of filters obvious to one skilled in the art include high-pass filters, low-pass filters, band-pass filters, and band-stop filters.

5. The signal is converted from analog to digital form to enable the processing of the signal by a computing apparatus 18 using an ADC 16. This example illustrates the use of a digital computing apparatus to perform part of the invention method; however, a digital computing apparatus is used as an example and does not limit the invention. Examples of the computing apparatus 18 include analog circuits, digital circuits, microprocessors and microcontrollers. Examples of currently used microcontrollers include Hitachi H8/3887, Texas Instruments 3185265-F, Sierra SC84036CV, Amtel S5640 ASIC, NEC FTA-R2 ACIC, Hitachi H8/3847, Panasonic MN101C097KB1, ASIC (built around Intel 8051), etc.

6. The signal is filtered using a filtering process 20. Such a filter may be used to reshape and/or transform the signal to a more optimal waveform that is better suited for the other computational processes in the computing apparatus 18. One example of such a filter may be a band-pass filter that just selects a particular range of frequencies and suppresses other frequencies from the measured signal. Such a filter would be useful if the current signal were generated by a nonlinear electrochemical process, resulting in higher frequency components in addition to the fundamental frequency that was used as the voltage stimulus.

7. The spectral content of the signal is characterized in teems of both the magnitude and phase angle of each frequency component of interest using a spectral analysis process 22; a commonly used process is the FT and includes related processes such as the FFT, DFT, WT, DTFT. One of ordinary skill will recognize the possibility of using other spectral analysis processes as appropriate for the system under consideration.

8. The signal contribution from ESSs that give rise to capacitive properties of the system in the measured signal is determined using a capacitive property quantification process 24. For example, one embodiment of such a process 24 is:

a. Compute the high frequency signal spectrum and quantify the relevant features of this portion of the spectrum, since the high frequency portion of the spectrum is expected to contain more information about the capacitive properties of the signal. In one example, the magnitude and phase angle of the frequency spectrum are used as the features of the signal.

b. Compute the values associated with capacitive properties of the signal; such properties may include but are not limited to the impedance, the reactance, the resistance, and the capacitance, utilizing any external data source A 26 that may be necessary.

9. Compute other values that may be derived from the above computations using a derived quantity computation process that may make reference to an external data source B 30. Data source A 26 and data source B may be the same data source. They represent means of storing information and can be different data structures within a single memory unit. Examples of information that the external data source B 30 may contain include properties of the transducer such as the electrode area and frequency response curves for different applications; properties of the sample such as the ionic strength, viscosity, density, double-layer capacitance values, and dielectric constant; properties of any material in the sample that may cause electrode fouling such as dielectric constants and related values; properties such as dielectric constants or thickness or capacitive properties of any membrane or similar material that may cover the electrode. Examples of derived quantities include computing the concentration of the analyte by comparison to calibration data, computing the effective electrode area, computing the extent of electrode fouling, and computing the dielectric and permittivity constants of the background electrolyte by comparison to equations and other data describing the composition of the electrolyte.

10. The derived quantities from the derived quantity computation process 28 are used in a correction process 40 that corrects for distortions or variations the measured signal 36 caused by environmental variations and physical variations which have been identified and quantified above. An example of a correction process is to scale the estimated analyte concentration that was determined by the derived quantity computation process 28 by a value that reflects the change in effective electrode area or by a value that reflects the extent of electrode fouling, as determined by the capacitive property quantification process 24.

11. The output 32 is generated in a usable form. Examples include transmitting the concentration values of all ESSI in electronic format or displaying the estimated analyte concentration in an LCD display to the user of the sensor.

FIGS. 5 and 6 refer to the processes that are implemented in the system of FIG. 7. Referring to FIG. 5, a waveform shape may be selected (step 100) and applied to an electrode system to measure samples containing known concentrations of the analyte of interest. In the first example embodiment, the electrode area is varied systematically with no electrode fouling as different concentrations of analyte are measured (steps 105, 110, 115, 120, 125) to gather calibration data. In the second example embodiment, the electrode area is kept constant, but the extent of electrode fouling is varied, as different concentrations of analyte are measured (steps 105, 110, 130, 135, 140) to gather calibration data.

In these example embodiments, the stimulus waveform is selected (step 100) so that a signal component that depends on the concentration of the desired analyte and a signal component that depends on environmental factors are measured. In this example, the two environmental factors that are illustrated are the effective electrode area and the extent of electrode fouling. According to an embodiment, the stimulus waveform is chosen such that the capacitive properties of the electrochemical system are extractable (step 110) and quantifiable. In an another embodiment, the stimulus waveform is chosen such that the capacitive signal components are much more sensitive to the environmental factors (e.g. electrode area and electrode fouling) and much less sensitive to the analyte concentration, thereby allowing for monitoring the effects of electrode area or electrode fouling that is independent of analyte concentration. This allows for quantification of just the environmental variation without dependence on the analyte concentration.

According to an embodiment that corrects for variations in effective electrode area, calibration data may be gathered by making measurements with electrodes of different known effective areas with samples containing known different analyte concentrations (step 115). For measurements made with each electrode area, calibration curves may be constructed that relate the Faradaic signal component to the concentration of the analyte in the sample (step 120). Calibration curves may also be constructed that relate the capacitive signal component to variations in electrode area when measuring samples with different analyte concentrations (step 120). In the system of FIG. 7, the filter process 20, spectral analysis process 22, and capacitive quantification process 24 can be used to quantify the capacitive signal component.

According to an embodiment, equations may be constructed to correct the calibration curve that estimates the analyte concentration based on a Faradaic signal component for errors that may arise from variations in the effective electrode area of the sensor using the capacitive calibration data that quantifies the effective electrode area (step 125).

Once the calibration curves and correction equations have been determined, in the system of FIG. 7, this information may be stored in data source A 26 and/or in data source B 30. The correction equations can be used in the correction process 40 to correct for an erroneous analyte estimate that has been altered by variations in the effective electrode area when a measurement is made in a sample of unknown analyte concentration and with an electrode where the effective electrode area is not known.

Referring to FIGS. 6 and 7, transducers 6 (illustrated as electrodes) may be placed into contact with the sample 2 containing unknown concentration of analyte, indicated by ESS 4. The selected stimulus waveform (step 105) may be applied to the electrodes by the potentiostat, indicated as the transducer control apparatus 12. The application of this stimulus waveform is illustrated as signal 34. The response signal 36 may be measured and analyzed by the computing apparatus 18 to quantify the capacitive and Faradaic signal components (step 110). The capacitive signal components, which have just been computed by spectral analysis process 22 and capacitive property quantification process 24, may be compared to calibration data stored in data source A 26 to determine effective electrode area (step 200). The Faradaic signal component may then be compared with calibration data from data source B 30 to estimate the analyte concentration in the sample (step 225).

This analyte estimate is not yet corrected for errors that may result from variations in effective electrode area. The correction equations from data source B 30 may be used with the initial analyte estimates in a correction process 40 to adjust the estimated analyte concentration to account for changes in effective electrode area (step 205). The corrected analyte estimate may then be output 32 in a usable form, such as using an LCD display (step 210).

According to an embodiment that corrects for variations in the extent of electrode fouling, calibration data may be gathered by making measurements with electrodes of different known extents of fouling with samples containing known different analyte concentrations (step 130). For these measurements, calibration curves may be constructed that relate the Faradaic signal component to the concentration of the analyte in the sample (step 135). Calibration curves may also be constructed that relate the capacitive signal component to variations in the extent of electrode fouling when measuring samples with different analyte concentrations (step 135). In the system of FIG. 7, the filter process 20, spectral analysis process 22, and capacitive quantification process 24 may be used to quantify the capacitive signal component.

According to an embodiment, equations are constructed to correct the calibration curve that estimates the analyte concentration based on a Faradaic signal component for errors that may arise from variations in the extent of electrode fouling using the capacitive calibration data that quantifies the extent of electrode fouling (step 140).

Once the calibration curves and correction equations have been determined, in the system of FIG. 7, this information may be stored in, for example, data source A 26 and/or in data source B 30. The correction equations may be used in the correction process 40, for example, to correct for an erroneous analyte estimate, such as one that has been altered by variations in the extent of electrode fouling when a measurement is made in a sample of unknown analyte concentration and with an electrode where the extent of fouling is unknown.

Referring to FIGS. 6 and 7, then, the electrode system (illustrated as transducers 6) may be placed into contact with the sample 2 containing unknown concentration of analyte (illustrated as ESS 4). The selected stimulus waveform (step 105) may be applied to the electrodes by the potentiostat (illustrated as transducer control apparatus 12). This waveform is illustrated as signal 34. The response signal 36 may be measured and analyzed by the computing apparatus 18 to quantify the capacitive and Faradaic signal components (step 110). The capacitive signal components, which have just been computed by spectral analysis process 22 and capacitive property quantification process 24, are compared to calibration data stored in data source A 26 to determine the extent of electrode fouling (step 215). The Faradaic signal component is compared with calibration data from data source B 30 to estimate the analyte concentration in the sample (step 225). This analyte estimate is not yet corrected for errors that may result from variations in the extent of electrode fouling. The correction equations from data source B 30 are used with the initial analyte estimates in a correction process 40 that adjusts the estimated analyte concentration to account for changes in the extent of electrode fouling (step 220). The corrected analyte estimate is then output 32 in a usable form, for example being displayed to the user in an LCD display (step 210).

In this example, the stimulus waveform is first used to gather calibration data from samples that contain different concentrations of analyte and with different environmental factors to form correction equations. This same waveform is applied to the sample containing unknown concentrations of the analyte and unknown environmental factors. In this example, ferrocyanide is identified as the desired (or target) analyte and effective electrode area and extent of electrode fouling are identified as illustrative environmental factors.

Figure 11:
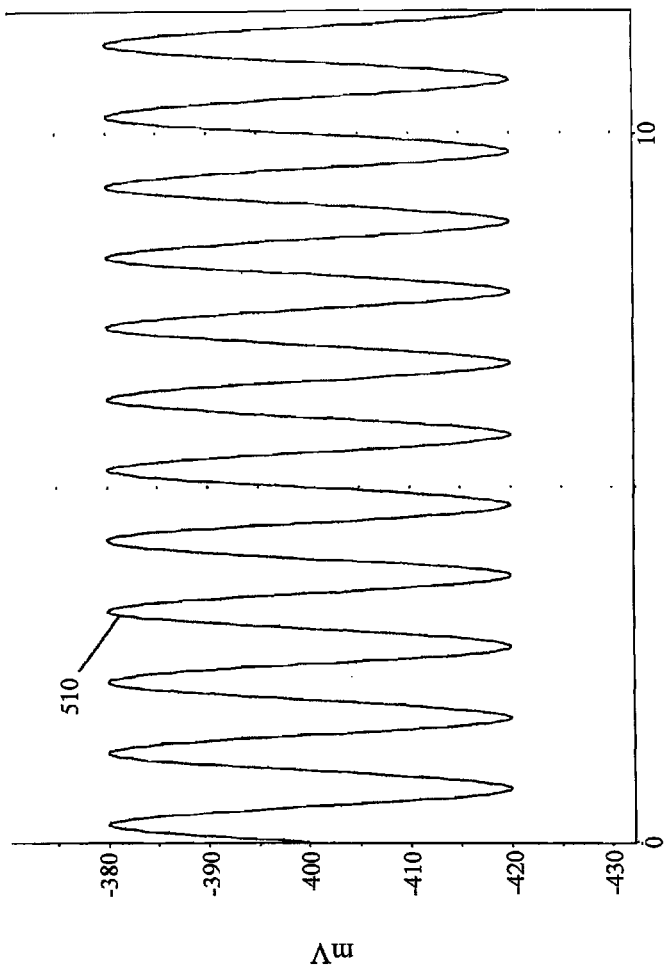
FIG. 11 shows a waveform applied to an electrode system in accordance with an example performed using the methods of FIG. 5 and FIG. 6.

The stimulus waveform may be a DC potential with a high frequency small amplitude AC sine wave superimposed. The phrase "high frequency small amplitude sine wave," as used herein, denotes a sinusoidal waveform (typically below 50 mV of peak-to-peak amplitude and typically above 100 Hz) that will generate a signal response from the sample that can be approximated by a linear relationship with the applied potential. A exemplary waveform format is shown in FIG. 11. A DC potential is applied to the electrode and an AC sinusoidal voltage 510 is superimposed onto this DC potential. The amplitude of this AC voltage 510 need not be kept below 50 mV and can be any value that gives rise to a usable signal. The frequency of the AC potential 510 may be adjusted as is needed to elicit the capacitive features of the electrochemical system, and the range may be adjusted as is needed for the system under consideration and does not limit the scope of the invention in any way. The AC voltage 510 may then be stepped through a range of frequencies to probe the spectral characteristics of the electrochemical system over a spectral range. One of ordinary skill in the art will recognize the possibility of using other waveforms that can extract capacitive properties of the electrochemical system including using different frequencies of stimulus and different shapes of waveforms.

The application of the DC and AC potentials may result in the generation of a DC and AC current, where the AC current may be comprised of the same frequency as the stimulating AC potential. If the electrochemical system is linear, then the resulting AC current will contain only the same frequency component as the stimulating AC potential. However, if the electrochemical system is not completely linear, then there may be other frequency components in the AC current signal.

At the stimulating frequency, the phasor representation of the voltage and current signals can be given by:

$$\vec{V} = V_r + jV_i$$

$$\vec{I} = I_r + jI_i$$

where $\vec{V}$ and $\vec{I}$ are vectors, called phasors, that represent the magnitude and phase angle information of the AC voltage and AC current signals, respectively, at a particular frequency of interest. The phasors represent this information as a complex number where the subscripts r and i represent the real and imaginary components, respectively. Furthermore, the magnitude and phase angle of the phasors can be given by:

$$\angle V = \arctan\left(\frac{V_i}{V_r}\right)$$

$$\angle I = \arctan\left(\frac{I_i}{I_r}\right)$$

$$|V| = \sqrt{(V_r)^2 + (V_i)^2}$$

$$|I| = \sqrt{(I_r)^2 + (I_i)^2}$$

The understanding with the use of phasors is that the information refers to a particular frequency of interest. Phasor analysis of sinusoidal signals is a well known method, as explained in B. P. Lathi, "Linear Systems and Signals", Berkeley-Cambridge Press, Carmichael, C A 1992. One example of using AC sine wave signals illustrates the use of probing the electrochemical system over a range of frequencies. According to an embodiment, an exemplary method of stepping through a range of frequencies may include the following steps:

1. Start the oscillation of the voltage at a particular frequency;
2. Record the resulting current signal when the readings stabilize;
3. Change the oscillation frequency to a new value; and
4. Repeat steps 2-4 as needed to cover the range of interest.

One example of stepping through a range of frequencies includes starting the oscillation at a particular frequency and then increasing the frequency logarithmically. However, one of ordinary skill in the art will recognize the possibility of starting at a higher frequency and decrementing the frequency through the desired range or the possibility of stepping through the frequencies in a linear fashion rather than a logarithmic fashion.

The spectral analysis process 22 can compute the necessary phasor information for the voltage and current signals according to an embodiment of the present invention. In one example, each frequency of stimulation is applied to the transducers in steps, so one possible method of spectral analysis is computing the phasor information for each frequency of stimulus subsequent to measurement at that frequency. Another example of a possible method is to store all the measured and applied signal data first and then perform all the computation in one step at the end of the data acquisition steps. Another example of a possible method is in the case of a linear electrochemical system, all the frequencies of interest may be superimposed simultaneously as the voltage stimulus; then the resulting current signal may be expected to contain responses at all the stimulating frequencies. Since that would be a case for a linear system, then performing a FT analysis on the entire signal at once would reveal the phasor information for each frequency of interest simultaneously. One of ordinary skill in the art will recognize the possibility of executing the spectral analysis process 22 in many different embodiments. For example, it may be possible to perform spectral analysis by measuring the correlation between the measured signal and a set of reference sinusoid waves of different frequencies and different phase shifts.

The phasor information for the current and voltage AC signals may then be used by the capacitive property quantification process 24. One method of quantifying the capacitive properties includes, but is not limited to, computing the immittance value of the electrochemical system. The immittance may be computed in terms of the impedance, given by $\vec{Z}$, or the admittance, given by $\vec{Y}$. In one example, the admittance is calculated as follows:

$$\vec{Y} = \frac{\vec{I}}{\vec{V}}$$

$$|\vec{Y}| = \frac{|\vec{I}|}{|\vec{V}|}$$

$$\angle \vec{Y} = \angle \vec{I} - \angle \vec{V}$$

$$\vec{Y} = \frac{1}{\vec{Z}}$$

where all values are taken to be given at a particular frequency.

The admittance values may be used for the computation of capacitive properties. An ideal capacitor as is traditionally considered in electronic circuit analysis will have the following admittance properties:

$$\vec{Y}(\omega) = j\omega C$$

$$|\vec{Y}(\omega)| = \omega C$$

$$\angle \vec{Y}(\omega) = 90°$$

where C is the capacitance, which describes the capacity of the system to store charge, j is the imaginary number $\sqrt{-1}$, and ω is the frequency of the sinusoidal stimulus, given by ω=2πf where f is the frequency in hertz.

An electrochemical system may also be a capacitive component, although the properties may not follow those of an ideal electronic capacitor. This capacitive property may arise from several considerations including, but not limited to the following:

1. placing an electrode in a sample that contains charged species approximates some of the electrical properties of an ideal electronic capacitor;
2. placing an electrode in a sample that contains ESSs which may have dipole moments that approximate some of the electrical properties of an ideal electronic capacitor; and
3. varying the electrode potential, or current, over time to approximate some of the electrical properties of an ideal electronic capacitor by allowing charge to accumulate on the electrode surface and thereby causing the accumulation of the appropriate charges near the electrode surface in the sample over time.

The origins of the capacitive properties of the electrode-sample interface 38 are well understood and are discussed in "Electrochemistry: Principles, Methods, and Applications", $1^{st}$ ed. Oxford University Press, 1993 by C. M. A. Brett and A. M. O. Brett. At high frequency measurements, the total electrochemical signal may be dominated by the capacitive components. Therefore, in this example, it is the high frequency spectrum that is considered for probing the capacitive properties of the electrochemical system.

The present invention encompasses several methods for computing the capacitance of the electrochemical system. One example is to obtain the current signal resulting from a high frequency sinusoidal potential waveform. The admittance values revealing the capacitive properties may not be ideal. Deviations from the ideal capacitor behavior may materialize in ways including, but not limited to, the admittance phase angle not being 90° in the range of frequencies measured. However, the admittance magnitude spectrum may still be linear when plotted on log-log axes, as is done in a Bode plot. These are examples of how the capacitive properties of an electrochemical system may be manifested in a real system and as such are intended to be examples for illustrative purposes and do not limit the scope of the invention.

Figure 12:
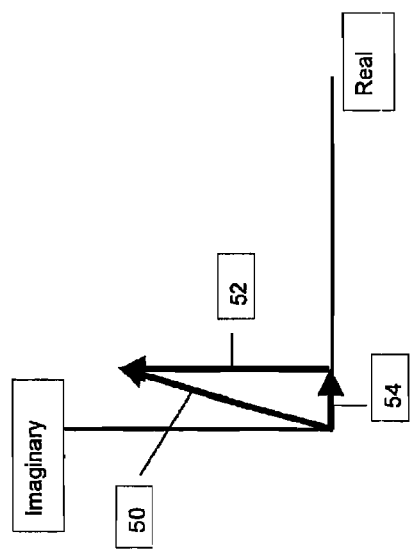
FIG. 12 shows how a vector in the complex plane can be decomposed into a real part and an imaginary part.

In analyzing the capacitive properties of an electrochemical system, the deviations from ideal capacitance may need to be considered. One example of how the variations may be addressed is to consider the component of the admittance that is at 90° for each frequency of interest. FIG. 12 illustrates this concept. At a particular frequency, the vector representing the admittance 50 is not the ideal capacitor value of 90°. However, the real component of the vector 54 and the imaginary component 52 can be used to deconstruct the total admittance vector 50 into two vectors. Therefore, by considering the value of the imaginary component 52 alone, the capacitive component of the total admittance may be selected. This allows for the extraction of just the current signal component that is 90° out of phase with the voltage signal, which can be a measure of the capacitive nature of the electrochemical system. In this way, non-ideal characteristics of the CDAS, which may cause deviations from the ideal 90° phase angle, can be minimized in the final analysis.

Another example of analyzing nonideal capacitive properties of an electrochemical system is to consider the magnitude spectrum. In this example, the magnitude spectrum in the frequency range that is dominated by capacitive signals is taken to be linear in a log-log Bode plot. As such, the linear nature of the magnitude plot may evince the dominance of capacitive components in the electrochemical system over non-capacitive components. In some applications, the slope of the magnitude spectrum may correlate to different properties of the TSI and can be used to characterize the system.

Some exemplary factors that may affect the capacitive properties of the electrochemical system include:
1. effective electrode area
2. components that comprise the sample including but not limited to ionic makeup of sample, non-ionic makeup of the sample, presence of various ESSs.
3. viscosity of the sample
4. density of the sample
5. extent electrode fouling
6. membranes which may cover the electrode
7. the applied DC voltage
8. the applied AC voltage
9. mass transport in the sample including, convection, diffusion of sample components, migration of sample components, flow rate of the sample
10. temperature
11. reactions which may occur at the electrode The measure of the capacitance of the electrochemical system may be used to probe characteristics of the electrochemical system. One example of how this may be embodied is by considering one equation that defines capacitance for a parallel plate capacitor:

$$C = \frac{A\varepsilon}{d}$$

where C is the magnitude of the capacitance, A is the area of the electrode, s is the permittivity (and reflects the dielectric properties of the system), and d is the distance between the plates of a parallel plate capacitor. In this example electrochemical system, one plate of the capacitor may be considered to be the electrode surface and the other plate may be considered to be the plane in the sample that contains the layer of spatially distributed charges. This is a well-known description of the TSI, commonly referred to as the "double-layer" and is discussed in "Electrochemistry: Principles, Methods, and Applications", $1^{st}$ ed. Oxford University Press, 1993 by C. M. A. Brett and A. M. O. Brett. One of ordinary skill in the art will recognize the possibility of having other equations relating the capacitance to the physical properties of the electrochemical setup. For example, a cylindrical capacitor equation may be more appropriate for a wire electrode. Such relationships that are necessary and appropriate for the system under consideration may be supplied by the data source A 26. Assuming the above equation to describe the capacitance of the electrochemical system under consideration in this example, it is possible to equate the admittance with the capacitance as follows:

$$|\vec{Y}(\omega)| = \omega C = \frac{\omega A \varepsilon}{d}$$

Thus, if the magnitude of the admittance is known at a given frequency, then there remain three unknowns, namely A, $\varepsilon$, and d. Utilizing an external data source A 26 which may contain the values of two of these unknowns, then the third may be computed by the above equation by the capacitive property quantification process 24. As a further example, the values of the parameters describing the capacitance need not be known explicitly. Instead, they may be known in aggregate and the change in capacitance due to one of these parameters may also be used as a measure of quantifying capacitive properties in process 24. The benefit of this analysis is that often several of these parameters may be known, but one may change without knowledge. This characteristic of the capacitance may be exploited to correct for variations in the TSI by a correction process 40.

These procedures that measure the capacitive properties of an electrochemical system may be useful due to the fact that the inherent nature of the measurements lends itself to monitoring primarily physical and material properties of the environments in which the electrochemical system operates. They help establish an overall metric for characterizing the physical and environmental effects of the electrochemical system and form the basis for developing correction mechanism 40 that can account for such sources of error and can be extended for more detailed measurements of various purposes, such as:

1. diagnosing the state and condition of an electrode or transducer, including determining effective electrode area
2. determining various characteristics of the electrode fouling scenario, including, but not limited to, the thickness of the fouling layer, the rate of fouling material buildup, and electrical properties of the fouling material.

In practice, a stimulus waveform can be selected through a combination of experimental trials and theoretical consideration of the processes that are involved in the detection process. The selection of the waveform is done in order to achieve certain unique signal characteristics generated by a particular analyte and the environmental factors. The DC component of the measured signal may be comprised mostly of Faradaic signal components, which are affected by the analyte concentration and environmental factors. But, the AC component of the measured signal may be comprised mostly of capacitive signal components, which are less likely to be affected by the analyte but are responsive to the environmental factors. Thus, the AC component may be used to independently gain information about the environmental factors without being influenced by the analyte concentration.

Factors to keep in mind when choosing a waveform include but are not limited to: the use of more positive potentials of the working electrode with respect to the reference electrode will generally increase the rate of oxidation; similarly, use of more negative potentials of the working electrode with respect to the reference electrode will generally increase the rate of reduction; and when the rate of kinetics is much faster than the rate of transport of the analyte (such as by diffusion), further increasing the rate of kinetics by increasing the potential in the appropriate direction (positive for oxidations or negative for reductions) may not significantly increase the Faradaic current flow; higher frequency AC sine waves may be sensitive to non-Faradaic capacitive properties than lower frequency AC sine waves.

After selecting the waveform, data may be gathered from samples containing different concentrations of the target and with different environmental factors (steps 115 and 130). For example, in distinguishing and determining the influence of effective electrode area and analyte concentration, one could make five repeated measurements using the selected waveform for each of the following concentrations of ferrocyanide: 0 mM, 1 mM, 2 mM, 3 mM, 5 mM, 10 mM, 15 mM, 20 mM using electrodes of each of the following effective areas: $0.1\ mm^2$, $0.2\ mm^2$, $0.3\ mm^2$, $0.5\ mm^2$, $0.7\ mm^2$, $10\ mm^2$. In another example, in distinguishing and determining the influence of the extent of electrode fouling and analyte concentration, one could make five repeated measurements using the selected waveform for each of the following concentrations of ferrocyanide: 0 mM, 1 mM, 2 mM, 3 mM, 5 mM, 10 mM, 15 mM, 20 mM using electrodes which have been coated with fouling material of each of the following thicknesses: 10 μm, 20 μm, 30 μm, 50 μm, 70 μm, 100 μm, 150 μm, 200 μm, 300 μm, 500 μm. Examples of materials that could be used to emulate different types of fouling include polymers such as cellulose acetate, and polytyramine, or proteins such as bovine serum albumin.

Example 1

Figure 2:
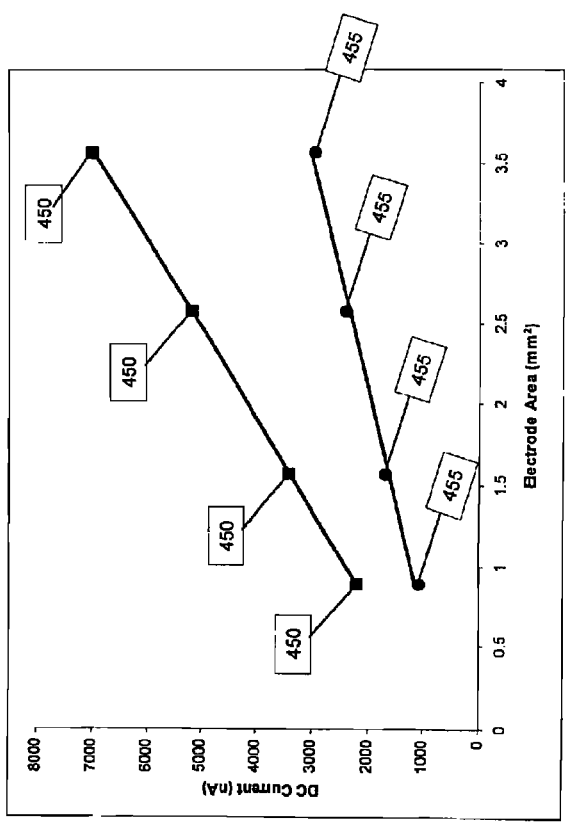
FIG. 2 is a chart showing the increase in DC current due to an increase in electrode area for two samples with different ferrocyanide concentration.

An example using the method of FIGS. 5 and 6 and system as carried out by, for example, a system of FIG. 7, is now described in terms of analyzing the concentration of a sample containing the analyte ferrocyanide and variable effective electrode area. The Faradaic reaction that is detected by a DC potential is given by:

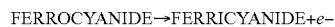
FERROCYANIDE→FERRICYANIDE+$e-$ which is an oxidation reaction. The electrochemical cell may be a conventional 3-electrode set up with a palladium working electrode, platinum counter electrode, and a Ag/AgCl reference electrode. The working electrode may be held at a DC potential of −400 mV with respect to the reference electrode. FIG. 2 shows the DC current from two samples, one containing 10 mM FERRO and the other containing 20 mM FERRO, for measurements made with different effective electrode areas.

Figure 10:
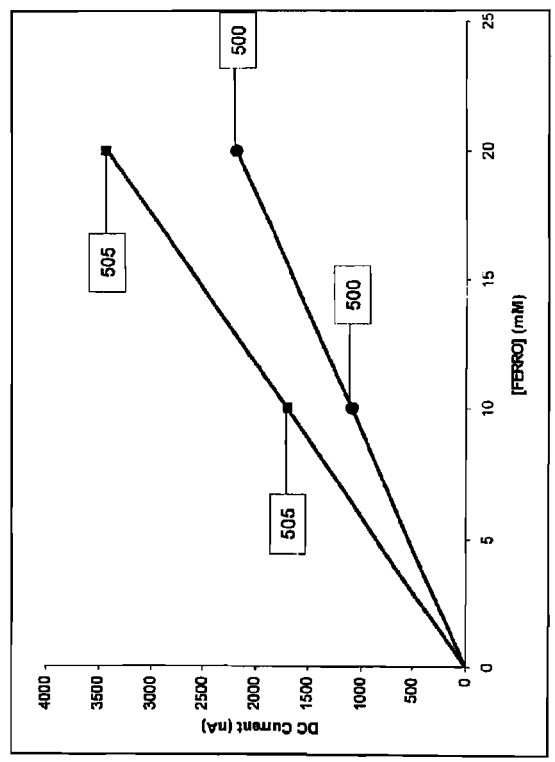
FIG. 10 shows calibration curves for ferrocyanide obtained with electrodes of two different effective areas.

FIG. 2 shows the data points 450 that were measured by applying a DC potential of −400 mV to a sample containing 20 mM ferrocyanide. Measurements 450 were made with electrodes of different effective areas, and the data is plotted in FIG. 2. The X-axis shows the effective electrode area of the electrode that was used to make the measurements and the Y-axis shows the value of the DC current that was measured. Using the same electrodes, measurements were then performed in samples containing 10 mM ferrocyanide and are shown as data points 455. This figure illustrates the problem of measuring amperometric signals using a DC potential. The measured signal is affected by both the analyte concentration and the effective electrode area. One equation that may be used to describe this relationship is:

$$I = \alpha A_e [FERRO]$$

where $\alpha$ is a proportionality constant, $A_e$ is the effective electrode area, and [FERRO] is the concentration of ferrocyanide in the sample. One of ordinary skill in the art would recognize the possibility of other relationships that may exist, and these relationships could be determined by a combination of theoretical and experimental investigation. FIG. 10 illustrates this relationship for two values of $A_e$. Data points 500 are the DC current measurements made with an electrode of $A_e = 0.8925$ mm². The equation of the calibration curve for this $A_e$ is:

$$I = 109.21 [FERRO]$$

Data points 505 are the DC current measurements made with an electrode of $A_e = 1.575$ mm². The equation of the calibration curve for this $A_e$ is:

$$I = 171.13 [FERRO]$$

Thus, if measurements are made with an electrode under the assumption that $A_e = 1.575$ mm², the ferrocyanide concentration would be estimated with the equation:

$$[FERRO] = I/171.13$$

where I is the measured DC current in nA and [FERRO] is the estimated ferrocyanide concentration in mM.

However, if the effective electrode area were unknowingly not equal to 1.575 mm², then the calculated ferrocyanide estimate could be incorrect. For example, if $A_e$ was actually 0.8925 mm², then a sample containing 20 mM ferrocyanide would yield a measured current signal of 2188 nA, as shown in FIG. 10 by data points 500. Examples of how such a change in $A_e$ might occur include errors in manufacturing or partial contact of the sample with the electrode. Using the assumption that $A_e$ is 1.575 mm², the estimated ferrocyanide concentration would be calculated by the calibration equation as:

$$[FERRO] = 2188/171.13 = 12.3 \text{ mM}$$

This illustrates the type of error in estimating analyte concentration that may occur if the effective electrode area were to become altered unknowingly. However, being able to obtain a measure of the effective electrode area would allow for correcting the analyte estimate for such changes in the measurement system.

To probe the effective electrode area, in this example a 1000 Hz sine wave of 40 mV peak to peak amplitude was superimposed onto the DC bias potential of −400 mV (step 100), as shown in curve 510 of FIG. 11. This waveform was then applied to the electrode system (step 105). The Fourier Transform of the resulting current signal was taken to select the 1000 Hz AC sinusoidal component (step 110), since the capacitive properties of the system are expected to be reflected in high frequency components of the signal. In this example, since the amplitude of the AC sine wave potential is kept constant at 40 mV peak to peak, it is sufficient to just use the AC current values in the calculation of capacitive properties instead of computing the admittance values, as is defined by the mathematical relationship between AC admittance, AC current, and AC potential discussed above.

Figure 13:
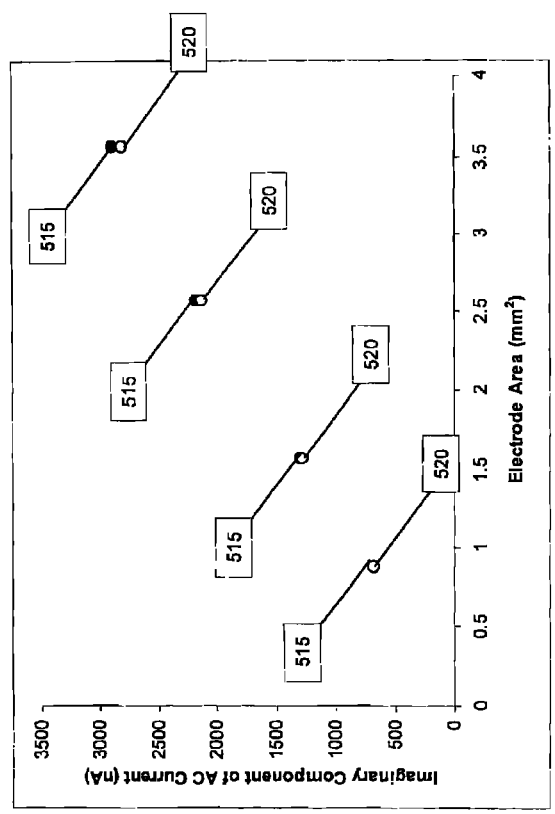
FIG. 13 is a chart showing the increase of the imaginary component of the AC current with increasing electrode area from measurements made from two samples containing different concentrations of ferrocyanide.

FIG. 13 shows capacitive signal data represented by the imaginary component of the 1000 Hz AC current signal gathered with electrodes of different effective areas in a sample of 10 mM ferrocyanide (black data points 515) and a sample of 20 mM ferrocyanide (white data points 520). It is clear from this data that there is a linear relationship between the capacitive signal component and the effective electrode area and that furthermore, the capacitive signal data is not significantly influenced by the concentration of ferrocyanide in the sample.

An equation that relates the imaginary AC current to the effective electrode area (step 120) that is independent of analyte concentration is:

$$I_{i,AC} = (818.26)(A_{e,actual}) - 14.33$$

where $I_{i,AC}$ is the imaginary component of the AC current at 1000 Hz, $A_{e,actual}$ is the actual effective electrode area.

One equation that may be used to describe the measured Faradaic DC electrode current ($I_F$) to be used in constructing calibration curves for estimating ferrocyanide concentration in a sample is:

$$I_F = \alpha A_{e,expected}[FERRO]$$

$$[FERRO] = \left(\frac{1}{\alpha A_{e,expected}}\right) I_F$$

where $A_{e,expected}$ is the value of the effective electrode area that the electrode is expected to have. This is because when calibration curves were constructed by using an electrode system (step 120) based on Faradaic signal data to relate measured Faradaic signal to ferrocyanide concentration, an electrode of effective area $A_{e,expected}$ was used. If an unknown sample is measured with an electrode of $A_{e,expected}$, and these calibration curves are used to estimate the ferrocyanide concentration in the sample (step 225), then one may expect that the estimated ferrocyanide concentration is representative of the actual concentration in the sample. However, if the unknown sample is measured with an electrode of effective area that is not equal to $A_{e,expected}$, then an erroneous estimate of ferrocyanide may likely result.

Thus, one correction equation (step 125) that may be used to adjust the estimated ferrocyanide concentration (step 205) for variations in the effective electrode area is:

$$[FERRO]_c = \left(\frac{1}{\alpha A_{e,expected}}\right)\left(\frac{A_{e,expected}}{A_{e,actual}}\right) I_F$$

$$[FERRO]_c = \left(\frac{A_{e,expected}}{A_{e,actual}}\right)[FERRO]_u$$

$$A_{e,actual} = \frac{I_{i,AC} + 14.33}{818.26}$$

where $A_{e,actual}$ is computed as described above. $[FERRO]_c$ is the ferrocyanide concentration corrected for variation in the effective electrode area and $[FERRO]_u$ is the uncorrected ferrocyanide concentration.

Continuing with the illustrative example, if calibration curves for estimating ferrocyanide concentration were constructed with an expected electrode area of that $A_{e,expected}$=1.575 mm$^2$, and measurements were made in a sample containing 20 mM ferrocyanide using an electrode with $A_{e,actual}$=0.8925 mm$^2$, an erroneous estimate of ferrocyanide concentration would result, as discussed above, giving [FERRO]=2188/171.13=12.3 mM. However, using the capacitive signal data, represented by the imaginary component of the 1000 Hz AC sinusoidal current, the estimated ferrocyanide concentration may be corrected for the variation in effective electrode area. As shown in FIG. 13 by data point 515, a sample containing 20 mM ferrocyanide measured by an electrode with $A_{e,actual}$=0.8925 mm$^2$ yields $I_{a,AC}$=680 nA. Thus, $$A_{e,actual} = \frac{I_{i,AC} + 14.33}{818.26} = \frac{680 + 14.33}{818.26} = 0.850 \text{ mm}^2$$

$$[FERRO]_c = \left(\frac{A_{e,excepted}}{A_{e,actual}}\right)[FERRO]_u = \left(\frac{1.575}{0.850}\right)12.3 = 22.8 \text{ mM}$$

thereby yielding a corrected estimate of 22.8 mM ferrocyanide as compared to an uncorrected estimate of 12.3 mM ferrocyanide, representing nearly a three-fold reduction of error.

This illustrates one exemplary embodiment that uses capacitive signal information to correct for measurement errors arising from variations in effective electrode area. Although this example was illustrated with one frequency of sine wave, improvements to this method may be realized by using information from multiple frequencies of sinusoidal stimuli, covering a range of frequencies to construct a set of correction equations to be used. Another example of an improvement is to construct calibration curves with a larger matrix of data. FIGS. 10 and 13 illustrated calibration data from samples that contained two different concentrations of ferrocyanide; however, calibration data may be acquired from samples comprised of a larger selection of different concentrations of ferrocyanide to create a more refined set of calibration curves. Similarly, data may be acquired from electrodes with many more different effective areas to create a more refined set of calibration curves.

Example 2

An example using the method of FIGS. 5 and 6 and system as carried out by, for example, a system of FIG. 7, is now described in terms of analyzing the concentration of a sample containing the analyte ferrocyanide and variable extent of electrode fouling. As in Example 1, the Faradaic reaction that is detected is the oxidation of ferrocyanide to ferricyanide, and an equivalent 3-electrode electrochemical system is used where the working electrode is a platinum electrode of 3.14 mm$^2$. In this example, the effective electrode area may be kept constant and the extent of electrode fouling is varied to illustrate the effect of fouling on the measured signal and the estimated ferrocyanide concentration. A method is described to use capacitive signal information to correct for errors in ferrocyanide estimation that may arise due to electrode fouling The working electrode was fouled by coating the whole electrode area with a cellulose acetate ("CA") membrane. The extent of electrode fouling was varied for two cases. In one case, CA was dissolved in acetone in the proportion of 10 mg cellulose acetate per 1 mL acetone. One µL of this solution was drop-coated onto the working electrode so as to cover the entire platinum surface. The solution was allowed to dry, forming a coating of cellulose acetate, giving a total of approximately 10 µg of CA. In a second case, CA was dissolved in acetone in the proportion of 3.33 mg CA per 1 mL acetone. One µL of this solution was drop-coated onto the working electrode so as to cover the entire platinum surface. The solution was allowed to dry, forming a coating of CA that contained approximately ⅓ the amount of cellulose acetate, approximately 3.33 µg CA. Thus, in this example, the amount of CA was varied to emulate different extents of electrode fouling; the expectation being that a greater extent of electrode fouling may be emulated by coating the electrode with a greater amount of cellulose acetate.

Figure 3:
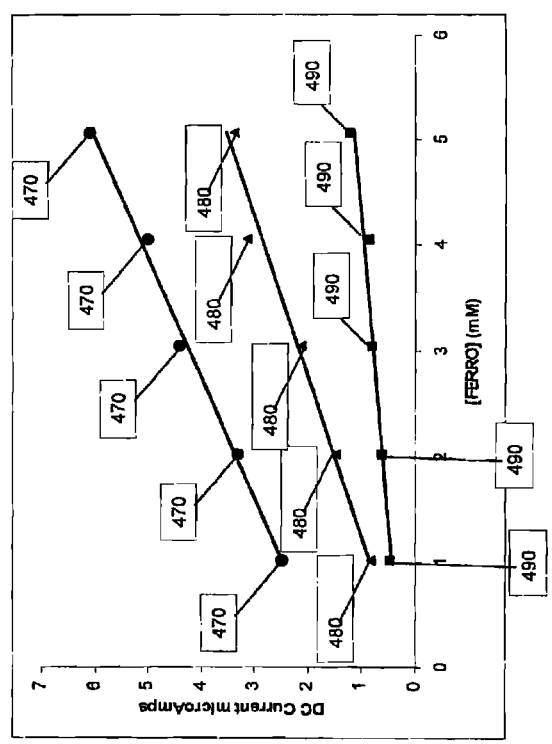
FIG. 3 is calibration curves showing the increase in DC current due to increasing concentration of ferrocyanide using three electrodes with different extents of fouling.
Figure 4:
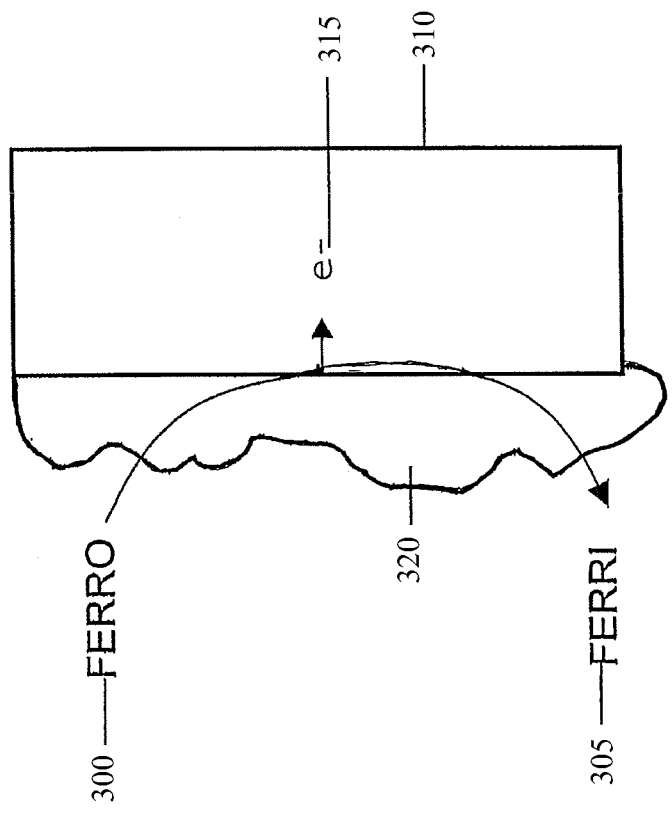
FIG. 4 is an amperometric sensor for measuring ferrocyanide where the electrode is fouled.

FIG. 3 shows calibration curves that were constructed by applying a DC potential of −400 mV to a sample containing different concentrations ferrocyanide using an electrode with no fouling (data points 470), 3.33 µg CA of fouling (data points 480), and 10 µg CA of fouling (data points 490). It can be seen that the measured DC current signal, which is dominated by the Faradaic current component from the oxidation of ferrocyanide, depends on both the concentration of ferrocyanide and the extent of electrode fouling. One equation of the calibration curve that may be used to describe this relationship is:

$I_{DC} = \alpha E_{f1} A_e [FERRO] + \beta E_{f2}$ where $\alpha$ and $\beta$ are constants, $A_e$ is the effective electrode area, $E_{f1}$ is a measure of how the extent of electrode fouling affects the slope of the calibration curve, $E_{f2}$ is a measure of how the extent of electrode fouling affects the intercept of the calibration curve, $I_{DC}$ is the measured DC current, and [FERRO] is the concentration of ferrocyanide in the sample. One of ordinary skill in the art would recognize the possibility of other relationships that may exist, and these relationships could be determined by a combination of theoretical and experimental investigation.

In the example of no fouling (data points 470), one equation that describes the calibration curve may be given as:

$I_{DC}$=0.8757[FERRO]+1.6

$A_e$=3.14 mm$^2$ $\alpha E_f$=0.279 µAmm$^{-2}$ mM

In the example of 3.33 µg CA of fouling (data points 480), one equation that describes the calibration curve may be given as:

$I_{DC}$=0.664[FERRO]+0.1717

$A_e$=3.14 mm$^2$ $\alpha E_f$=0.211 µAmm$^{-2}$ mM

In the example of 10 µg CA of fouling (data points 490), one equation that describes the calibration curve may be given as:

$I_{DC}$=0.1729[FERRO]+0.2703

$A_e$=3.14 mm$^2$ $\alpha E_f$=0.055 µAmm$^{-2}$ mM

Figure 15:
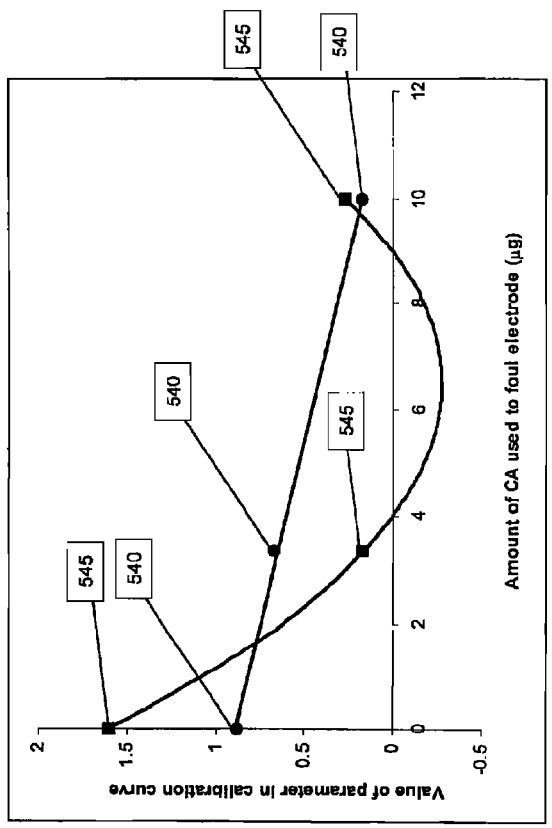
FIG. 15 shows how the relationship between the slope and intercept of a calibration curve, that relates concentration of ferrocyanide to DC current, depends on the extent of electrode fouling.

It can be seen that the extent of electrode fouling affects both the slope and the intercept of the calibration curves. FIG. 15 is an example of how the relationship between the extent of electrode fouling and the parameters of the linear calibration curve, which in this example are the slope and intercept, can be expressed. Data points 540 represent the value of the slope of the calibration curve that relates [FERRO] to $I_{DC}$ for different extents of electrode fouling, given by the quantity $\alpha E_{f1} A_e$; data points 545 represent the value of the intercept of the calibration curve that relates [FERRO] to $I_{DC}$ for different extents of electrode fouling, given by the quantity $\beta E_{f2}$. One example set of equations to describe these relationships is:

$$I_{DC} = \alpha E_{f1} A_e [FERRO] + \beta E_{f2}$$

$$\alpha E_{f1} A_e = -0.0708(M_{CA}) + 0.8853$$

$$\beta E_{f2} = 0.0444(M_{CA})^2 - 0.5767(M_{CA}) + 1.6$$

where $M_{CA}$ is the mass of CA used to foul the electrode in micrograms. One of ordinary skill will recognize that other equations and relationships may be used, depending on the nature of the data.

Figure 14:
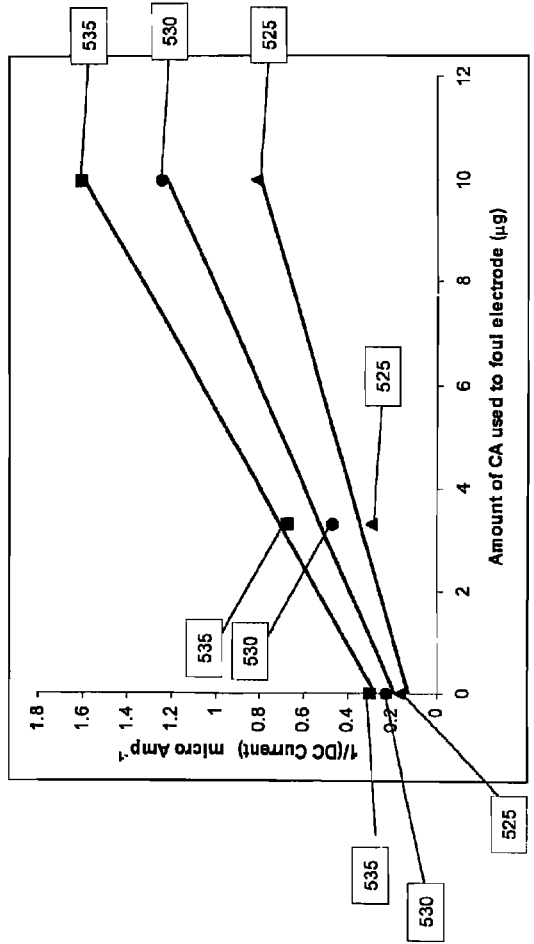
FIG. 14 is a chart showing the dependence of the DC current on the extent of electrode fouling from three samples containing different amounts of ferrocyanide.

FIG. 14 further illustrates the relationship between the measured current, ferrocyanide concentration, and the extent of electrode fouling for three concentrations of ferrocyanide using electrodes with three different extents of fouling. Data points 525 are from samples containing 5 mM ferrocyanide, data points 530 are from samples containing 3 mM ferrocyanide, and data points 535 are from samples containing 2 mM ferrocyanide. The data are plotted in FIG. 14 with the Y-axis representing the reciprocal of the measured DC current. In this example, such a representation allows for an approximately linear relationship to be observed between the amount of CA used to foul the electrode and the measured DC current. One of ordinary skill will recognize that other relationships may exist, depending on the nature of the electrochemical system and the nature of the fouling. In the example data illustrated in FIG. 14, the relationship between the DC current and the extent of fouling may be given as:

$$\frac{1}{I_{DC}} = 0.1317 M_{CA} + 0.275$$
$$I_{DC} = \frac{1}{0.1317 M_{CA} + 0.275}$$ for samples with 2 mM ferrocyanide;

$$\frac{1}{I_{DC}} = 0.1033 M_{CA} + 0.1871$$
$$I_{DC} = \frac{1}{0.1033 M_{CA} + 0.1871}$$ for samples with 3 mM ferrocyanide;

$$\frac{1}{I_{DC}} = 0.067 M_{CA} + 0.1279$$
$$I_{DC} = \frac{1}{0.067 M_{CA} + 0.1279}$$ for samples with 5 mM ferrocyanide;

where $I_{DC}$ is the DC current in microamps and $M_{CA}$ is the mass of CA used to foul the electrode in micrograms.

Thus, if measurements are made with the assumption that there is no electrode fouling, then the calibration curve representing this case could be used. However, if the electrode is fouled to an unknown extent, then an incorrect ferrocyanide estimate may be computed. For example, if the electrode were fouled by 3.33 μg of CA and measurements were made in a sample containing 5 mM ferrocyanide, then according to FIG. 14, $I_{DC}$=3.4 μA. Since, in this example, the extent of electrode fouling is not known or quantified, the calibration curve that is used to estimate ferrocyanide concentration is the one constructed with data from an unfouled electrode, as described above. Using this calibration curve, the following inaccurate estimate of ferrocyanide concentration is obtained:

$$I_{DC} = 0.8757[FERRO] + 1.6$$

$$[FERRO] = \frac{I_{DC} - 1.6}{0.8757} = \frac{3.4 - 1.6}{0.8757} = 2.1 \text{ mM.}$$

Thus, a method is needed to quantify the extent of electrode fouling so that the calibration curve parameters of slope and intercept may be altered to more accurately estimate the ferrocyanide concentration in the sample. To probe the extent of electrode fouling, a 1000 Hz sine wave of 40 mV peak to peak amplitude was superimposed onto the DC bias potential of −400 mV (step 100), as shown in curve 510 of FIG. 11. This waveform was then applied to the electrode system (step 105). In this example, since the capacitive properties of the system are expected to be the dominant component in the high frequency part of the signal, the peak to peak amplitude of the AC current signal was computed (step 110) by taking the difference between the peak of the sine wave current and the valley of the sine wave current for the last full measured cycle.

Figure 16:
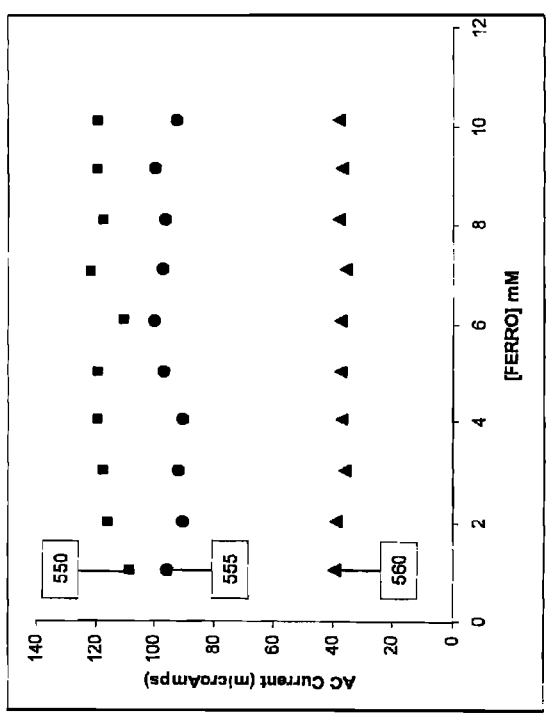
FIG. 16 is a chart showing the amplitude of the AC current for different concentrations of ferrocyanide as measured with three electrodes with different extents of fouling.
Figure 17:
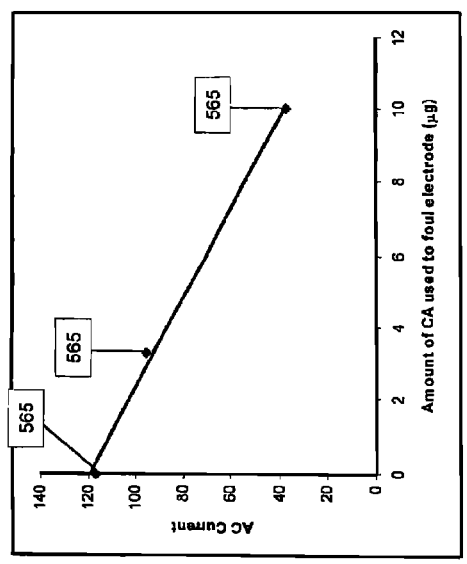
FIG. 17 shows the value of the AC current for measurements made with electrodes with different extents of fouling.

FIG. 16 shows capacitive signal data represented by the peak to peak amplitude of the 1000 Hz AC current signal gathered from samples with different concentrations of ferrocyanide using electrodes with no fouling (data points 550), 3.33 μg of CA used to foul the electrode (data points 555), and 10 μg of CA used to foul the electrode (data points 560). It is clear from this data that the AC current amplitude is mostly affected by the extent of fouling and minimally affected by ferrocyanide concentration. Thus, the average value of the AC current was calculated for each set of measurements made with a fixed extent of electrode fouling. FIG. 17 shows that in this example, there is a linear relationship between this average AC current amplitude (data points 565) and the extent of electrode fouling. One calibration equation to describe the relationship between the extent of electrode fouling and the AC current is given by:

$$I_{AC} = (-8.0598)(M_{CA}) + 119.05$$

where $I_{AC}$ is the peak to peak amplitude of the 1000 Hz sinusoidal current component and $M_{CA}$ is the mass of CA used to foul the electrode.

The AC measurements may be insensitive to and independent of analyte concentration in this example. So, the AC current value may be used to estimate the extent of electrode fouling. Once the extent of electrode fouling has been estimated, a correction to the concentration calibration curve may be made to result in a more accurate estimate of ferrocyanide concentration.

Continuing with the example of measuring a sample containing 5 mM ferrocyanide with an electrode that has been fouled by 3.33 μg of CA, according to FIG. 16, an AC current of 96.8 μA would be recorded. Using the calibration curve that relates AC current to mass of CA, the following estimate of mass of CA is obtained:

$$I_{AC} = (-8.0598)(M_{CA}) + 119.05$$

$$M_{CA} = \frac{I_{AC} - 119.05}{-8.0598} = \frac{96.8 - 119.05}{-8.0598} = 2.76 \text{ μg.}$$

Using this estimated mass of CA as a measure of electrode fouling, the correction factors to the calibration curve slope and intercept may be determined using the equations described above:

$$\alpha E_{f1}A_e = -0.0708(M_{CA}) + 0.8853 = -0.0708(2.76) + 0.8853 = 0.690$$

$$\beta E_{f2} = 0.0444(M_{CA})^2 - 0.5767(M_{CA}) + 1.6 = 0.044(2.76)^2 -$$
$$0.5767(2.67) + 1.6 = 0.346$$

$$I_{DC} = \alpha E_{f1}A_e[FERRO] + \beta E_{f2}$$

$$[FERRO]c = \frac{I_{DC} - \beta E_{f2}}{\alpha E_{f1}A_e} = \frac{3.4 - 0.346}{0.690} = 4.4 \text{ mM}$$

where [FERRO]c is the estimate of ferrocyanide in the sample that has been corrected for the extent of electrode fouling. The corrected estimate of ferrocyanide is thus 4.4 mM; when compared to the uncorrected estimate of 2.1 mM, the correction method represents nearly a 5-fold reduction of error.

This illustrates one example embodiment that uses capacitive signal information to correct for measurement errors arising from variations in the extent of electrode fouling. Although this example was illustrated with one frequency of sine wave, improvements to this method may be realized by using information from multiple frequencies of sinusoidal stimuli, covering a range of frequencies to construct a set of correction equations to be used. Another example of an improvement is to construct calibration curves with a larger matrix of data. FIGS. 14, 15, 16, and 17 illustrate calibration data from electrodes with three extents of fouling; however, calibration data may be acquired from electrodes with a greater selection of different extents of fouling to create a more refined set of calibration curves. Similarly, data may be acquired from samples containing many more different concentrations of ferrocyanide to create a more refined set of calibration curves. Another example of an improvement is to use the imaginary part of the AC current signal, since the imaginary part of the AC signal is expected to reflect the capacitive properties of the electrochemical system.

Example 3

Another example of a useful benefit of capacitance measurements is detecting when the sample changes. There may be situations in fuel tank storage where foreign material leaks into these tanks, as shown in FIG. 19. For example, it is not uncommon for water to seep into a fuel tank that contains petrol products. In some situations, the water and petrol are immiscible and each liquid separates into layers within the tank. This is shown in the figure by a layer of petrol 56 with a layer of water 58 on top. There may be a layer of air space 60 above that as well. If an array of electrodes 62, 64, 66, 68, 70, 72, 74 were lined along the side of the tank, then it may be possible to spatially resolve the distribution of the water layers within the petrol layers. One way in which this may be embodied is that by measuring the capacitance of each electrode system 62, 64, 66, 68, 70, 72, 74 by measuring the CDAS. In one example, this can be achieved by applying small amplitude high frequency sine waves to the electrode system and measuring the resulting current. The AC current component will contain capacitive information about the electrochemical system. By referencing external data 30 which contains the CDAS profiles for a petrol sample and a water sample, then the derived quantity computation process 28 can determine which set of electrodes were in contact with water samples 72 and 70 and which electrodes were in contact with the petrol samples 62, 64, 66, 68, and which electrodes were not in contact with either 74. This can then allow for spatially resolving the amount of water seepage into a petrol storage tank. In this example, it may be estimated that approximately one part of water for two parts of petrol by volume are in the tank since two sensors 72 and 70 are in contact with water 58 and four sensors 62, 64, 66, 68 are in contact with petrol 56.

One of ordinary skill in the art will also recognize the possibility of using other sources of data in computing the values of capacitance-related properties of an electrochemical system. One example includes generating a database of capacitance values for different electrode configurations and sample configurations. For example, it may be possible to develop a set of admittance spectra for:

1. different ionic strengths of background electrolyte in a given sample;
2. different thicknesses of a particular membrane or part of a membrane that covers an electrode;
3. different thicknesses of material that may foul an electrode;
4. different samples;
5. different electrode geometry.

One of ordinary skill in the art will also recognize the possibility of using other signal parameters to obtain capacitive information about the electrochemical system. One example includes the initial rate of decay of a measured signal in response to a step potential. Another example is the amount of hysteresis that is observed when the electrochemical technique of cyclic voltammetry is used.

FIG. 18 shows an illustrative embodiment of a glucose meter that can be used to implement the various methods described above. The meter includes a test strip connector 600 to connect the test-strip to the meter. The test strip can include, for example, three electrodes (working, reference, and counter).

Signal conditioning circuitry 602 is coupled to the test strip connector 600, and performs filtering of the waveform applied to the electrodes in the test strip. Signal conditioning circuitry 604 performs filtering of the resultant current signal from the test strip, and records the current signal. Circuitry 602 and 604 together comprise what is known as a potentiostat circuit. DAC 606 converts digital signals from controller 610 to analog signals. ADC 608 converts analog signals into digital format for use by controller 610. Controller 610 processes signals in the meter, for example, by processing current signals sensed by test strip connector in the manner taught in the foregoing illustrative embodiments of FIGS. 5 and 6.

Buttons 612 provide a user interface for the user to operate the meter. Power circuit 614 provides power to the meter, usually in the form of batteries, and LCD 616 displays the glucose concentration to the user.

It should be noted that the format of the FIG. 18 meter, and the signal processing systems and methods taught herein in FIGS. 5-7, can be used to sense analytes other than glucose. Such applications include: electrochemical immunoassay sensing, industrial gas sensing, water quality monitoring (biological or toxic metals), sensing of chemical and biological warfare agents.

The signal processing techniques taught herein can also be applied to existing sensing devices, such as a existing glucose testers. This modification can be in the form of a firmware upgrade to existing controllers.

The function of the firmware upgrade is to implement the following signal processing techniques taught herein:

1) Applying a customized waveform to the sample. The data that encodes the shape of the waveform may reside in memory, will be read by the microprocessor, and the desired waveform may be generated and applied to a digital to analog converter, e.g., DAC 606 of FIG. 18.

2) Read in the resulting current signal. The firmware may instruct the microprocessor to read in the digitized data from the analog to digital converter (sensed from the test strip electrodes), e.g., ADC 608 of FIG. 18, and store the digitized data in memory. The firmware may perform the memory management that is needed to read in the desired data.

3) Perform the mathematical operations to implement the signal processing. This includes calculating the parameters according to the firmware's instructions (e.g., compute the Fourier Transform of the signals), and using these parameter values in the estimation equation (e.g., generated by the methods of FIG. 5 or FIG. 6) to determine the glucose concentration.

Other processes performed by the firmware may be left to the existing firmware and do not need to be part of the upgrade. For example, the firmware may also control the display of a result to the user (via the LCD 616 display, for example), and other "behind the scenes" operations of the meter, e.g., power management, respond to user requests such as scrolling of data, averaging of data, transferring data to a PC, etc.

It will be apparent to those skilled in the art that additional various modifications and variations can be made in the present invention without departing from the scope or spirit of the invention.

Other embodiments of the invention will be apparent to those skilled in the art from consideration of the specification and practice of the invention disclosed herein. It is intended that the specification and examples be considered as exemplary only, with a true scope of the invention being indicated by the following claims.

The invention claimed is:

1. A method for determining effective electrode area in an electrochemical test cell containing a liquid sample, wherein the electrochemical test cell comprises two electrodes and the effective electrode area is the area of the electrodes that is in contact with the liquid sample, said method comprising:
    applying a potential stimulus to the electrodes to generate a current signal, the potential stimulus comprising a time-varying potential component superimposed on a constant potential component;
    isolating a time-varying current component from the current signal;
    determining a phase angle of the time-varying current component relative to the time-varying potential component;
    using the phase angle to separate the time-varying current component into a real component and an imaginary component, the magnitude of the imaginary part being related to the effective electrode area; and
    determining effective electrode area from the determined magnitude of the imaginary part of the time-varying current component.

2. The method of claim 1, wherein the effective electrode area changes as a result of electrode fouling.

3. The method of claim 2, wherein the measured extent of electrode fouling is used to adjust the measured current signal and correct for signal distortion caused by electrode fouling.

4. The method of claim 3, wherein the adjustment corrects for a decrease in signal intensity due to fouling.

5. The method of claim 1, wherein the measured effective electrode area is used to adjust the computation of concentration of an analyte and correct for signal distortion caused by changes in effective electrode area.

6. The method of claim 5, wherein the adjustment is based on relative changes from initial analyte estimates.

7. The method of claim 5, wherein the adjustment is based on reference to an external data source.

8. The method of claim 7, wherein the external data source comprises calibration curves from calibration data gathered from electrodes having different electrode areas.

* * * * *

UNITED STATES PATENT AND TRADEMARK OFFICE
CERTIFICATE OF CORRECTION

PATENT NO. : 9,572,524 B2
APPLICATION NO. : 14/919935
DATED : February 21, 2017
INVENTOR(S) : Iyengar et al.

It is certified that error appears in the above-identified patent and that said Letters Patent is hereby corrected as shown below:

In the Specification

Column 8, Line 17 should read: -- terms of both the magnitude and phase angle of each --

Column 15, Line 2 should read: -- of the electrode, ε is the permittivity (and reflects the --

Column 15, Line 32 should read: -- A, ε, and d. Utilizing an external data source A 26 which --

Signed and Sealed this
Eleventh Day of April, 2017

Michelle K. Lee
*Director of the United States Patent and Trademark Office*